(12) United States Patent  
Yassinzadeh

(10) Patent No.: US 10,376,255 B2  
(45) Date of Patent: *Aug. 13, 2019

(54) BILATERAL VESSEL CLOSURE

(71) Applicant: Cardiva Medical, Inc., Santa Clara, CA (US)

(72) Inventor: Zia Yassinzadeh, San Jose, CA (US)

(73) Assignee: Cardiva Medical, Inc., Santa Clara, CA (US)

( * ) Notice: Subject to any disclaimer, the term of this patent is extended or adjusted under 35 U.S.C. 154(b) by 86 days.

This patent is subject to a terminal disclaimer.

(21) Appl. No.: 15/155,884

(22) Filed: May 16, 2016

(65) Prior Publication Data

US 2016/0256142 A1 Sep. 8, 2016

Related U.S. Application Data

(63) Continuation of application No. 13/016,073, filed on Jan. 28, 2011, now Pat. No. 9,370,347.

(Continued)

(51) Int. Cl.
*A61B 17/12* (2006.01)
*A61B 17/00* (2006.01)
*A61M 25/10* (2013.01)

(52) U.S. Cl.
CPC .... *A61B 17/0057* (2013.01); *A61B 17/12045* (2013.01); *A61B 17/12136* (2013.01);
(Continued)

(58) Field of Classification Search
CPC .......... A61B 17/0057; A61B 17/12045; A61B 17/12136; A61B 2017/0065;
(Continued)

(56) References Cited

U.S. PATENT DOCUMENTS 572,551 A 12/1896 Lesser
4,790,315 A 12/1988 Mueller, Jr. et al.
(Continued)

FOREIGN PATENT DOCUMENTS

GB 0905751.4 4/2009

OTHER PUBLICATIONS

Notice of allowance dated Feb. 17, 2016 for U.S. Appl. No. 13/016,073.

(Continued)

*Primary Examiner* — Robert A Lynch
(74) *Attorney, Agent, or Firm* — Wilson Sonsini Goodrich & Rosati

(57) ABSTRACT

A system for sealing a large penetration in the wall of a femoral artery comprises an occlusion catheter and an applicator. An access catheter may further be provided in order to facilitate introduction of the occlusion catheter. The occlusion catheter is introduced through a contralateral penetration, advanced over the aortic bifurcation, and an occlusion element on the occlusion catheter is positioned at the large diameter penetration. The occlusion element is then inflated to temporarily seal the large penetration while blood perfusion past the occlusion element is provided by the catheter. A sealing material, such as a tissue adhesive or other hemostatic agent is then introduced into a tissue tract above the large diameter penetration in order to seal the penetration. The occlusion element may be left in place while the sealing material has time to set, cure or otherwise form a permanent seal of the large penetration. The occlusion catheter and all access sheaths may then be removed from the patient.

20 Claims, 7 Drawing Sheets

Related U.S. Application Data

(60) Provisional application No. 61/303,058, filed on Feb. 10, 2010.

(52) U.S. Cl.
CPC .................. *A61B 2017/0065* (2013.01); *A61B 2017/00654* (2013.01); *A61B 2017/00676* (2013.01); *A61B 2017/12127* (2013.01); *A61M 2025/1052* (2013.01); *A61M 2025/1095* (2013.01)

(58) Field of Classification Search
CPC ........... A61B 2017/00654; A61B 2017/00676; A61B 2017/12127; A61M 2025/1052; A61M 2025/1095
See application file for complete search history.

(56) References Cited

U.S. PATENT DOCUMENTS

| | | | |
|---|---|---|---|
| 5,222,974 | A | 6/1993 | Kensey et al. |
| 5,725,551 | A * | 3/1998 | Myers ................ A61B 17/0057 604/285 |
| 5,785,679 | A | 7/1998 | Abolfathi et al. |
| 5,795,331 | A | 8/1998 | Cragg et al. |
| 6,056,769 | A | 5/2000 | Epstein et al. |
| 6,190,857 | B1 | 2/2001 | Ralph et al. |
| 6,989,022 | B2 | 1/2006 | Nowakowski |
| 7,008,442 | B2 | 3/2006 | Brightbill |
| 7,169,168 | B2 | 1/2007 | Van et al. |
| 9,370,347 | B2 | 6/2016 | Yassinzadeh |
| 2004/0044358 | A1 | 3/2004 | Khosravi et al. |
| 2004/0267308 | A1 | 12/2004 | Bagaoisan et al. |
| 2005/0004660 | A1 | 1/2005 | Rosenbluth et al. |
| 2006/0200075 | A1 | 9/2006 | Zadno-Azizi |
| 2008/0125715 | A1 | 5/2008 | Cohen |
| 2010/0324429 | A1 * | 12/2010 | Leschinsky ........ A61B 5/02208 600/493 |
| 2012/0029436 | A1 | 2/2012 | Yassinzadeh |

OTHER PUBLICATIONS

Office action dated Jan. 28, 2015 for U.S. Appl. No. 13/016,073.
Office action dated Feb. 12, 2014 for U.S. Appl. No. 13/016,073.
Office action dated Feb. 27, 2013 for U.S. Appl. No. 13/016,073.
Office action dated May 22, 2014 for U.S. Appl. No. 13/016,073.
Office action dated Aug. 27, 2014 for U.S. Appl. No. 13/016,073.
Office action dated Sep. 10, 2015 for U.S. Appl. No. 13/016,073.
Office action dated Nov. 2, 2012 for U.S. Appl. No. 13/016,073.

* cited by examiner

BILATERAL VESSEL CLOSURE

CROSS-REFERENCE

This application is a continuation of U.S. application Ser. No. 13/016,073, filed Jan. 28, 2011, which claims the benefit of U.S. Provisional Application No. 61/303,058, filed Feb. 10, 2010, the entire contents of which are incorporated herein by reference.

BACKGROUND OF THE INVENTION

1. Field of the Invention

The present invention relates generally to medical methods and apparatus. More particularly, the present invention relates to methods and apparatus for closing large arterial penetrations such as those formed for cardiac access during interventional procedures.

Angioplasty, atherectomy, drug delivery, stenting, and a variety of other interventional radiological procedures have proven to be of great benefit in the treatment of coronary artery disease. Such procedures are routinely performed by entering the femoral artery in a patient's groin and advancing an interventional catheter through a guiding catheter, over the aortic arch, and into the coronary arteries. Access to the femoral artery in the groin is typically achieved with an access sheath having a working diameter in the range from 4 Fr to 16 Fr, where one French equals 0.33 mm.

After the interventional procedure has been completed, the interventional and guiding catheters are removed, leaving the access sheath in place. The access sheath maintains hemostasis for as long as it is in place, and removal of the access sheath will result in bleeding from the femoral artery through the vessel wall penetration into the tissue tract from which the access sheath has been removed. A variety of protocols have been developed for closing the arterial wall penetration and sealing the access tract. Most simply and reasonably effectively for smaller diameter access penetrations, pressure may be applied on the patient's skin above the tissue tract and vessel wall penetration for sufficient time to permit coagulation, typically from 10 minutes to 30 minutes. While effective for smaller vessel wall penetrations, the need to employ a surgical nurse or other trained personnel to maintain pressure on the tissue tract and vessel during coagulation is very inefficient.

To improve the efficiency and reliability of the vessel wall closure, other techniques have been proposed. For example, devices have been developed for delivering hemostatic plugs through the vascular access sheath in order to promote hemostasis. Such apparatus are commercially available under the tradename Angio-Seal™ from St. Jude Medical, Inc., St. Paul, Minn. Other devices for suturing the vessel wall penetration through the tissue tract are available under the tradename Perclose® ProGlide™ from Abbott Vascular Devices, a division of Abbott Laboratories, Chicago, Ill. While such suture-based devices have been used to close large vessel penetrations, suturing can cause puckering of the vessel wall which can lead to an undesirable reduction in lumen size of the vessel. A third approach which is particularly advantageous since it leaves no suture or implant in the patient is available under the tradename Boomerang® Wire from Cardiva Medical, Inc., Sunnyvale, Calif. The Boomerang® Wire device provides for a temporary hemostasis after removal of the access sheath by expanding a small disk on the luminal side of the femoral wall penetration to allow natural clotting to occur in the tissue above the penetration.

While each of these approaches can be an improvement over applying manual pressure to the access site, they have proven to be less effective with very large access tracts and vessel wall penetrations such as those used in percutaneous valve repair and replacement. Those recently developed procedures require very large access penetrations and sheaths, often from 10 Fr to 24 Fr, and usually require bilateral penetration with a smaller access tract formed into the contralateral femoral artery. Access and closure of such large vessel penetrations are generally accomplished surgically by cutting down to the vessel. Percutaneous access and closure protocols are not routinely performed at present.

For these reasons, it would be desirable to provide improved and alternative techniques and systems for closing larger diameter femoral access tracts and vessel wall penetrations. It would be particularly desirable to provide such techniques and systems which may be employed with bilateral access protocols having at least one large diameter femoral wall penetration. At least some of these objectives will be met by the inventions described below.

2. Description of the Background Art

Vascular closure devices are described in U.S. Pat. Nos. 6,190,857; 7,169,168; and 6,056,769. See also US2006/0200075 and U.S. Pat. No. 7,008,442.

SUMMARY OF THE INVENTION

The present invention provides methods and systems for closing large penetrations in atrial walls at the end of a tissue tract. By "large penetration," it is meant that the penetration will accommodate an access sheath having an outside diameter of 10 Fr or larger, typically being 12 Fr or larger, often being as large as 16 Fr, 20 Fr, 24 Fr or even larger. Methods will be performed in patients having at least a second penetration in the wall of the same or a different artery or other blood vessel. Most commonly, the first, large penetration will be in a femoral artery and the second penetration will be in the contralateral femoral artery, i.e. the artery on the other side of the aortic bifurcation. Such bilateral femoral access is often used for performing cardiac procedures which require the use of relatively large interventional catheters as well as the use of two or more interventional catheters which may be introduced from the two femoral arteries. Such cardiac interventional procedures include percutaneous valve replacement, such as replacement of the aortic valve, and percutaneous valve repair, such as repair of the mitral valve. The vessel wall penetrations will be disposed at the distal end of a tissue tract which is formed from the patient's skin surface to the artery or other blood vessel. Such tissue tracts are typically formed by the Seldinger technique where the needle is used to access the artery or other blood vessel, the resulting tract dilated, and an access sheath left in place in the dilated tissue tract. The access sheath usually has a hemostasis valve at its proximal end so that interventional, diagnostic, or other catheters may be introduced through the valve into the artery and upward through the aorta and over the aortic arch until reaching the coronary vasculature.

The methods of the present invention will be performed after an interventional or other procedure has been completed, typically a cardiac interventional procedure requiring the first, large arterial penetration and a second, usually smaller, arterial penetration. The methods comprise advancing an occlusion catheter through the second penetration in the arterial or other vascular wall to position an occlusion element on a luminal side of the large penetration. The occlusion element is deployed temporarily to seal the large penetration while allowing blood perfusion past the occlusion element to limit the risk of ischemia in the tissue distal to the occlusion element. While maintaining the temporary seal on the large penetration, a sealant is introduced into the tissue tract above the occluded large penetration in order to effect closure and sealing of the large penetration.

In the exemplary methods of the present invention, the large penetration is formed in a first femoral artery and the second penetration is formed in the contralateral femoral artery. The occlusion catheter is initially advanced in a retrograde direction from the second penetration, through the contralateral femoral artery and over the aortic bifurcation. The catheter is then advanced in an antegrade direction through the first femoral artery until the occlusion element is positioned adjacent the large penetration. Usually, prior to introducing the occlusion catheter, an access catheter is advanced through the second penetration, over the aortic bifurcation, and into the first femoral artery. A flow diversion element on the access catheter is then typically deployed to inhibit blood flow from the aorta into the first femoral artery. The occlusion catheter may then be advanced through a lumen of the access catheter and past the deployed flow diversion element. The temporary blockage of the flow past the flow diversion element allows the flow occlusion element to be deployed with minimal disruption from blood flow through the femoral artery. Once the flow occlusion element is deployed, the flow diversion element may be taken down, allowing blood flow to flow through a perfusion path provided by the occlusion catheter, as described in greater detail below.

Typically, deploying the flow diversion element comprises inflating a balloon on a distal region of the access catheter within the first femoral artery in the region below the aortic bifurcation and above the large penetration. The access catheter will not provide perfusion or bypass flow since it is the purpose of the flow diversion element to temporarily stop blood flow although for a relatively short duration, typically less than one minute, while the flow occlusion element on the occlusion catheter is being deployed. Deploying the occlusion element typically comprises inflating a balloon on a distal region of the occlusion catheter. The occlusion catheter, in contrast to the access catheter, will be provided with a perfusion or bypass flow, typically through a passage disposed in the occlusion element having perfusion inlet port(s) and one or more outlet perfusion ports at the distal tip of the occlusion catheter.

Once the temporary occlusion of the large penetration has been established, a sealant will be injected or otherwise introduced into the tissue tract above the penetration. The occlusion element will prevent the sealant from entering the femoral or other blood vessel lumen, and the availability of perfusion allows the occlusion to be maintained for a time sufficient to permit setting, curing, activation of the clotting cascade, or other action or activity of the sealant to seal the tissue tract.

Introducing the sealant will typically comprise injecting an adhesive, releasing a thrombotic material, releasing a hemostatic plug, or otherwise introducing a material, substance, structure, or the like, which will form a seal in the tissue tract above the vessel wall penetration. The adhesive may comprise, for example, cyanoacrylate or a fibrinogen glue. Thrombogenic material include collagen and other biocompatible matrix materials having a thrombin component. The use of various hemostatic plugs and other tract-filling structures or compositions is well known in the medical arts. Such adhesives or other materials may be introduced or released using syringes, cannulas, catheters, or other tubes or devices which may be advanced at least partly down the length of the tissue tract, where the adhesive or other material is then released or advanced out of the device so that it remains within the tissue tract after the syringe, tube, or other injector is removed.

Systems according to the present invention for sealing a large penetration in a wall of a first femoral artery at the end of a tissue tract comprise an occlusion catheter and an applicator. The occlusion catheter carries an occlusion element near a distal end thereof, and the occlusion catheter is adapted to be advanced through a penetration in a contralateral femoral artery; i.e., the femoral artery on the opposite side of the aortic bifurcation with respect to the first femoral artery. The occlusion element is adapted to be positioned and deployed in the vessel, at the large penetration, to temporarily seal the large penetration. The system applicator is adapted to deliver a sealing material, such as a tissue glue, a thrombogenic material, a hemostatic plug or the like, into the tissue tract above the large penetration in the wall of the first femoral artery. The occlusion catheter will typically have a blood perfusion passage in at least a distal portion thereof. The blood perfusion passage permits blood to flow past the occlusion element when the occlusion element is deployed in the first femoral artery. Usually, blood perfusion passage will be connected to one or more inlet ports on a body of the occlusion catheter proximal to the occlusion element and one or more outlet port(s). Typically, the occlusion element comprises a balloon mounted on the distal region of the occlusion catheter, but other expansible membranes and blocking elements could also be provided, such as a blood impermeable membrane formed over an expansible cage or other mechanical element.

Systems of the present invention may further comprise an access catheter having a flow diversion element at a distal end thereof. The access catheter will also have a central passage which is adapted to receive the occlusion catheter therethrough. The access catheter will be further adapted to be advanced through the penetration in the contralateral femoral artery, over the aortic bifurcation, and into the first femoral artery to position the flow diversion element above the large penetration. Deployment of the flow diversion element will temporarily block blood flow from the aorta, through the first femoral artery, to the large penetration. The flow diversion element will typically comprise a balloon disposed coaxially on the access catheter above the central passage near a distal region thereof.

The access catheter and occlusion catheter will have dimensions which permit the access catheter to be first introduced from the second vascular penetration over the aortic arch to a region above the large penetration. Typically, the occlusion catheter will have a length in the range from 20 cm to 100 cm, usually from 30 cm to 80 cm, and an outside diameter in the range from 4 Fr to 9 Fr. The access catheter will usually have a length which is shorter than that of the occlusion catheter, typically being in the range from 15 cm to 90 cm, more usually from 25 cm to 70 cm, and an outside diameter in the range from 5 Fr to 10 Fr. The applicator may comprise a syringe or other delivery tube carrying an adhesive or a thrombogenic material, or may alternatively comprise a delivery tube carrying a hemostatic plug.

DETAILED DESCRIPTION OF THE INVENTION

Figure 1:
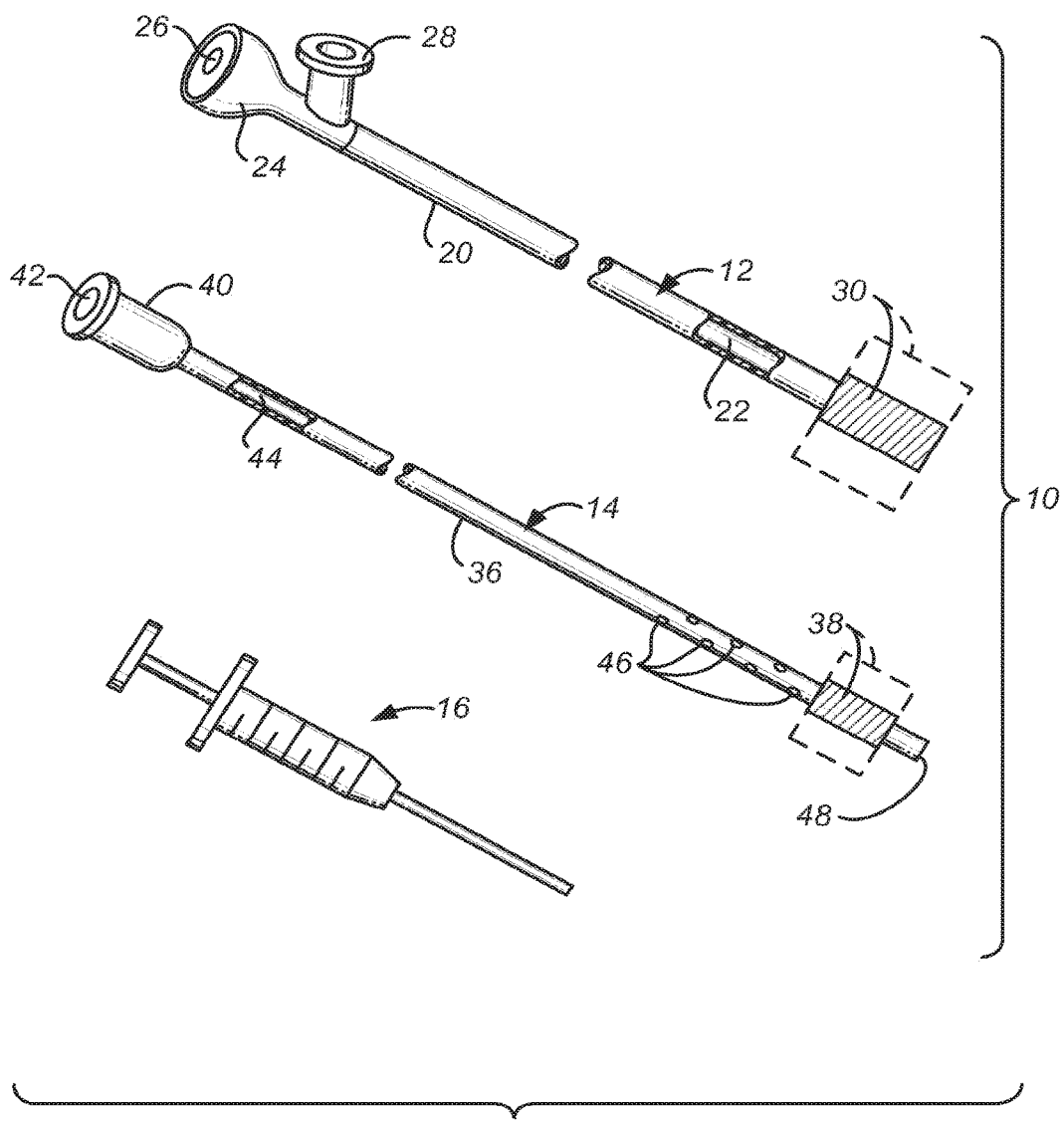
FIG. 1 illustrates a system constructed in accordance with the principles of the present invention, including an access catheter, an occlusion catheter, and an applicator for delivering a sealing material.

Referring to FIG. 1, a system 10 according to the present invention comprises an access catheter 12, an occlusion catheter 14, and an applicator 16 for delivering a sealing material to a tissue tract. The access catheter 12 comprises a shaft 20 having at least one central passage 22 for receiving and positioning the occlusion catheter 14 therethrough. A hub 24 includes a hemostatic valve 26 which permits introduction of the occlusion catheter 14 through the access catheter when the access catheter is present in the arterial vasculature. In particular, the hemostatic valve, which may have any one of a variety of conventional constructions, seals against the pressurized blood in the central passage 22 while permitting introduction of and/or removal of the occlusion catheter 14 therethrough. In addition to the central passage 22, the occlusion catheter shaft 20 will also have an inflation lumen (not shown) having an inflation port 28 on or adjacent the hub 24 and connected to a balloon flow diversion element 30 shown in its deflated configuration in full line and in its inflated configuration in broken line. The balloon flow diversion element 30 may be inflated by connecting a conventional balloon inflator to the inflation port 28.

Occlusion catheter 14 comprises an occlusion catheter shaft 36 having a balloon occlusion element 38 at a distal end thereof and a hub 40 including an inflation port 42 at its proximal end. The shaft 36 includes at least one lumen 44 connecting the inflation port 42 with the balloon occlusion element 38 so that the balloon occlusion element may be inflated from its deflated configuration (shown in full line) to its inflated configuration (shown in broken line). In addition, the occlusion catheter shaft 36 will include at lest a second lumen or passage (not shown) extending from a plurality of perfusion inlet ports 46 over a distal region thereof to at least one outlet port 48 at or near a distal tip thereof. The inflation lumen 44 will be isolated from the perfusion passage (not shown) so that the balloon may remain inflated while the perfusion passage remains available for perfusing blood from the inlet ports 46 to the outlet port 48, as will be described in more detail below. Occlusion element 38 may be inflated by injection of saline, or preferably contrast solution to allow for visualization.

The applicator 16 may take a variety of forms depending on the type of sealing material to be introduced. As illustrated in FIG. 1, applicator 16 comprises a syringe for delivering a liquid or other flowable sealant composition, such as a tissue glue or a thrombogenic material. Suitable tissue glues include cyanoacrylate, fibrin glues, and the like. Other deliverable sealing materials include thrombogenic materials, such as thrombin-containing substances. Still other sealing materials comprise plugs made from collagen or other matrix materials, where the collagen or matrix materials may further include thrombin, fibrin, or other clot-inducing materials. A variety of specific sealing materials and applicators for their delivery into tissue tracts are known in the art and would be useful in the inventions herein. Such applicators may include cannulas and pushers for advancing material, or other tubular elements for delivering liquids, gels, solids, and the like.

Figure 2:
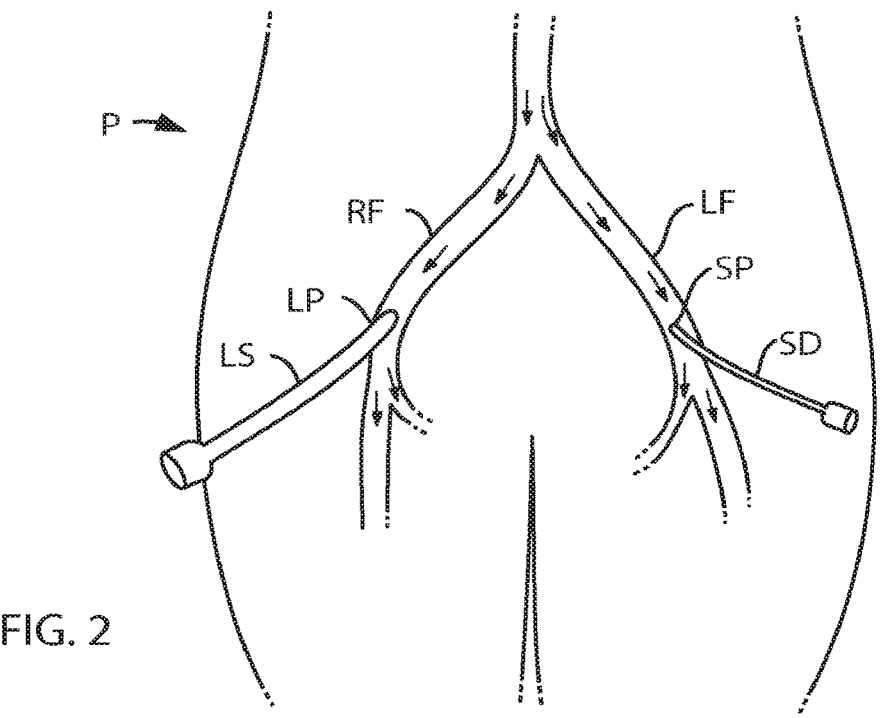
FIGS. 2-11 illustrate use of the system of FIG. 1 for delivering a sealant material to a tissue tract above a large penetration in a femoral artery.

Referring now to FIGS. 2-11, use of the system 10 for delivering a sealing material to a tissue tract over a femoral artery in accordance with the principles of the present invention will be described. In FIG. 2, the groin region of a patient P having a large diameter access sheath LS in a right femoral artery and a small diameter access sheath SD in a left femoral artery LF is shown. The interventional and/or diagnostic catheters have been removed from the access sheaths, and it will be assumed that whatever interventional procedure had been performed is over and that it is desired to close the vascular penetrations LP and SP.

Figure 3:
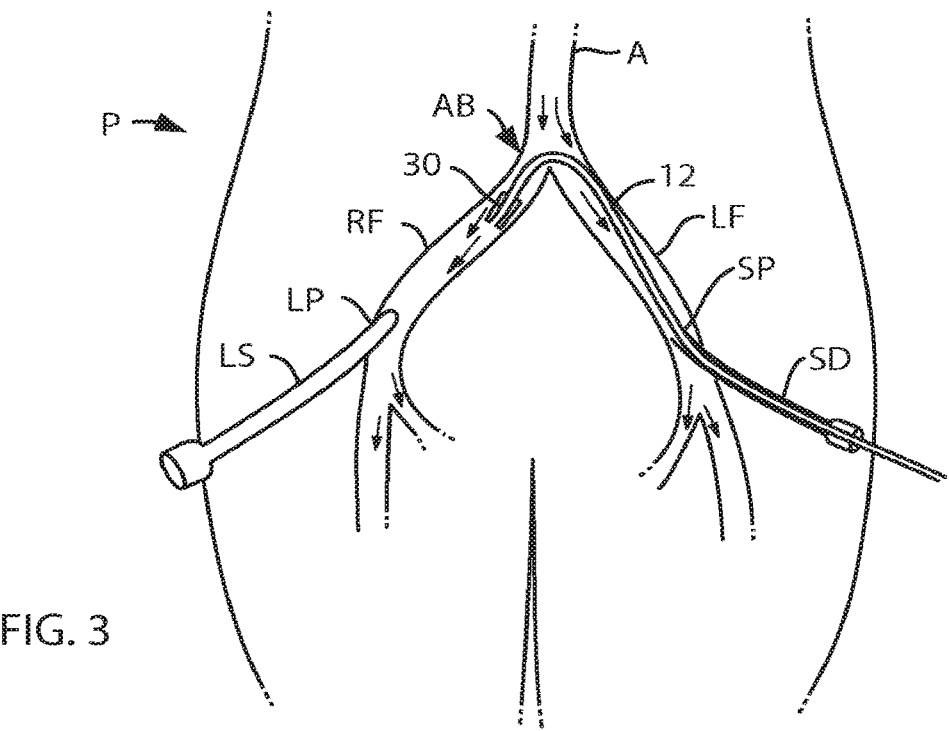

As shown in FIG. 3, the access catheter 12 is initially introduced through the small diameter access sheath SD through the small penetration SP so that the balloon flow diversion element 30 is positioned over the aortic bifurcation AB in the right femoral artery RF (which is contralateral to the left femoral artery LF), and above the large penetration LP. At this point, the balloon flow diversion element 30 is deflated and blood continues to flow downwardly from the aorta A into both the right femoral artery RF and left femoral artery LF.

Figure 4:
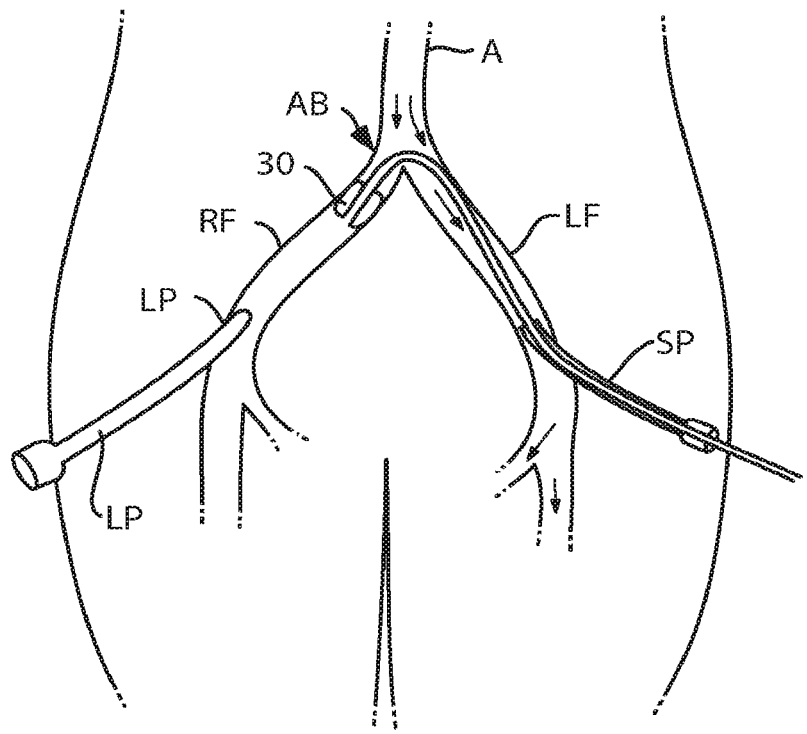

As shown in FIG. 4, the balloon flow diversion element 30 may be inflated to block blood flow into the right femoral artery RF, thus isolating the large penetration LP from high pressure arterial circulation. Blood continues to flow from the aorta A downward through the left femoral artery LF.

Figure 5:
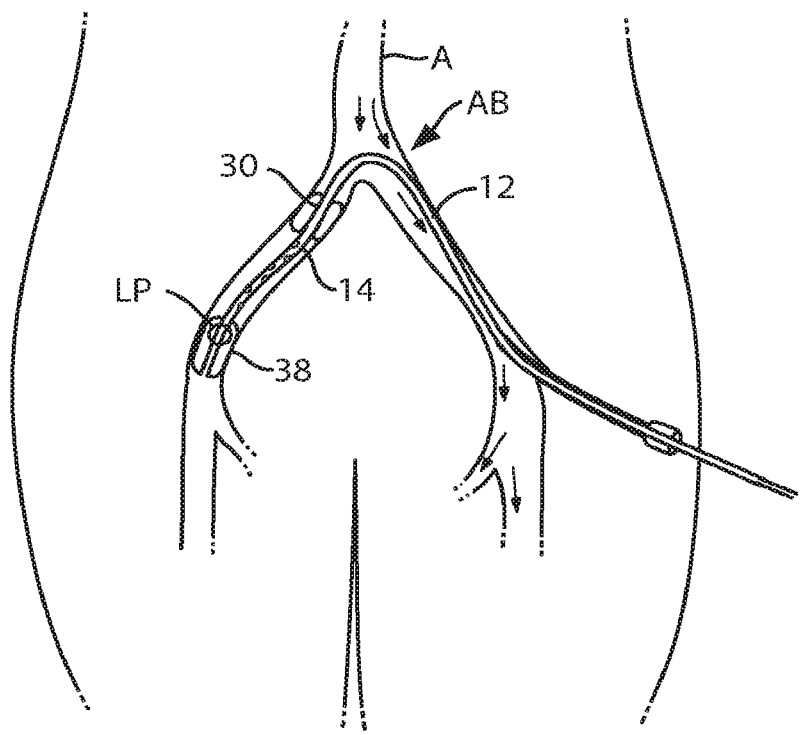

While the balloon flow diversion element 30 remains inflated, the occlusion catheter 14 is introduced through the central passage of the access catheter 12, and the balloon occlusion element 38 is positioned at the large penetration LP (FIG. 5). As the large penetration remains isolated from the high pressure vasculature, the large sheath can be removed so that the occlusion element 38 can be positioned immediately adjacent the penetration, as shown in FIG. 5. The occlusion element 38 may then be inflated to temporarily occlude the large penetration LP while the balloon flow diversion element 30 remains inflated.

Figure 6:
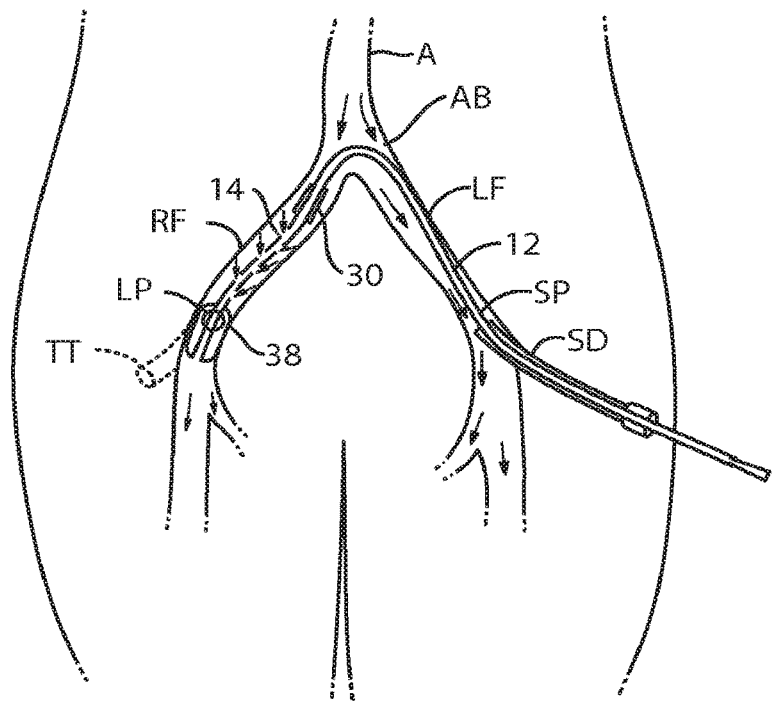
Figure 6A:
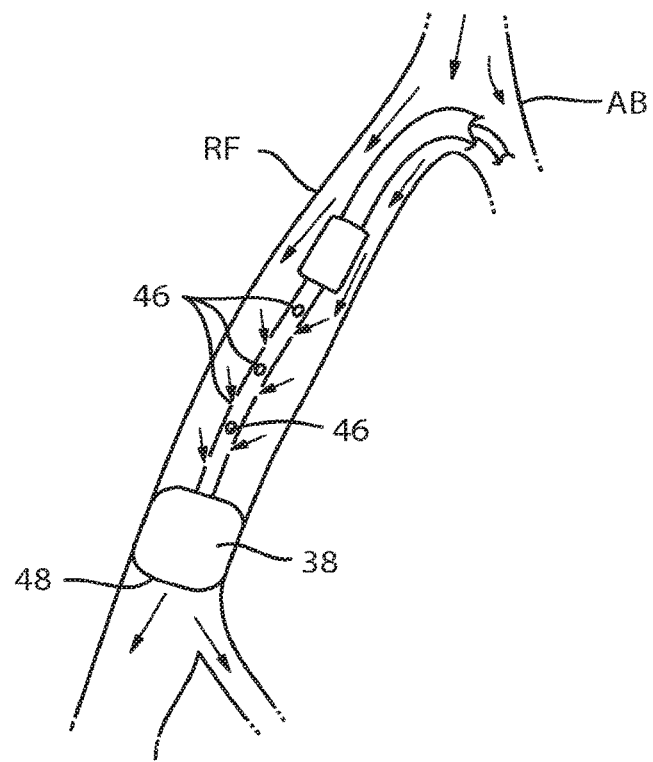
FIG. 6A is detailed view of the placement of the access catheter and occlusion catheter across an aortic bifurcation when positioning an occlusion element at a large diameter penetration.

As shown in FIG. 6, after the balloon occlusion element 38 has been inflated, the balloon flow diversion element 30 may be deflated, allowing blood to flow back in to the right femoral artery RF. As shown in the more detailed view of FIG. 6A, the blood flows down the right femoral artery RF and is able to pass into the perfusion inlet ports 46 and outwardly through the perfusion outlet port 48 while the balloon occlusion element 38 remains inflated.

Such perfusion is particularly advantageous since it reduces the risk of tissue ischemia distal to the occlusion balloon 38 during the remainder of the procedure.

Figure 7:
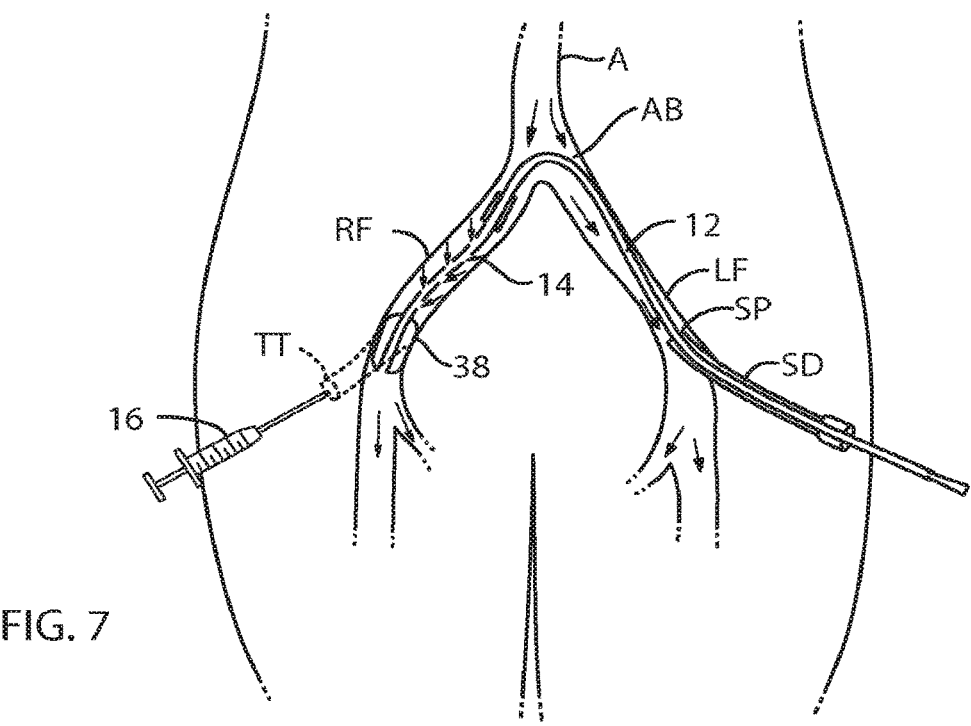
Figure 8:
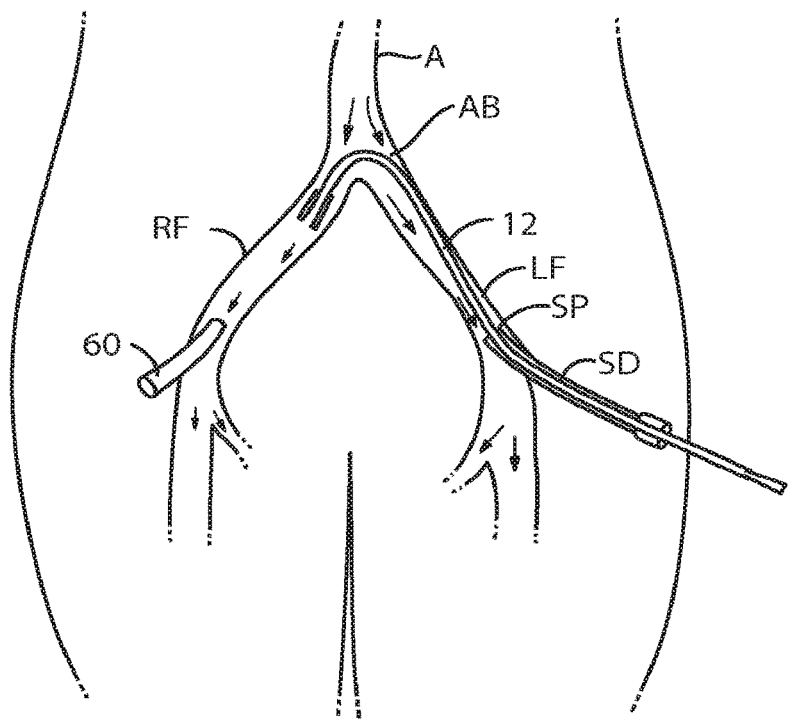
Figure 9:
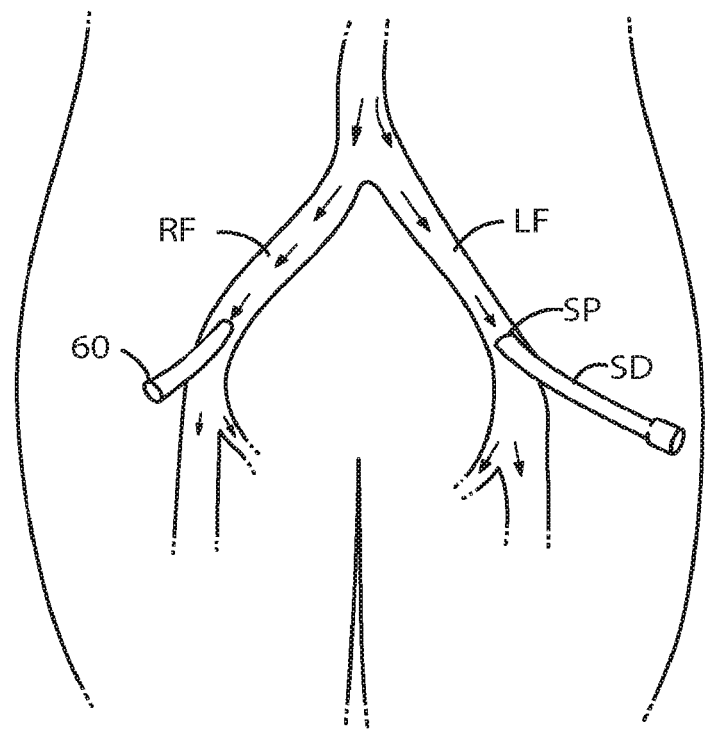
Figure 10:
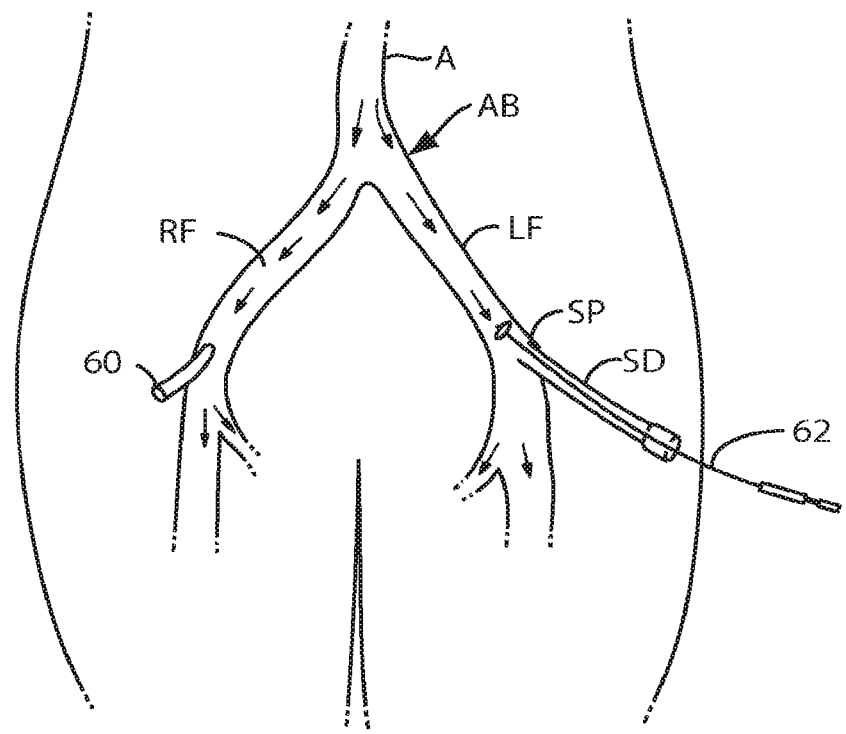
Figure 11:
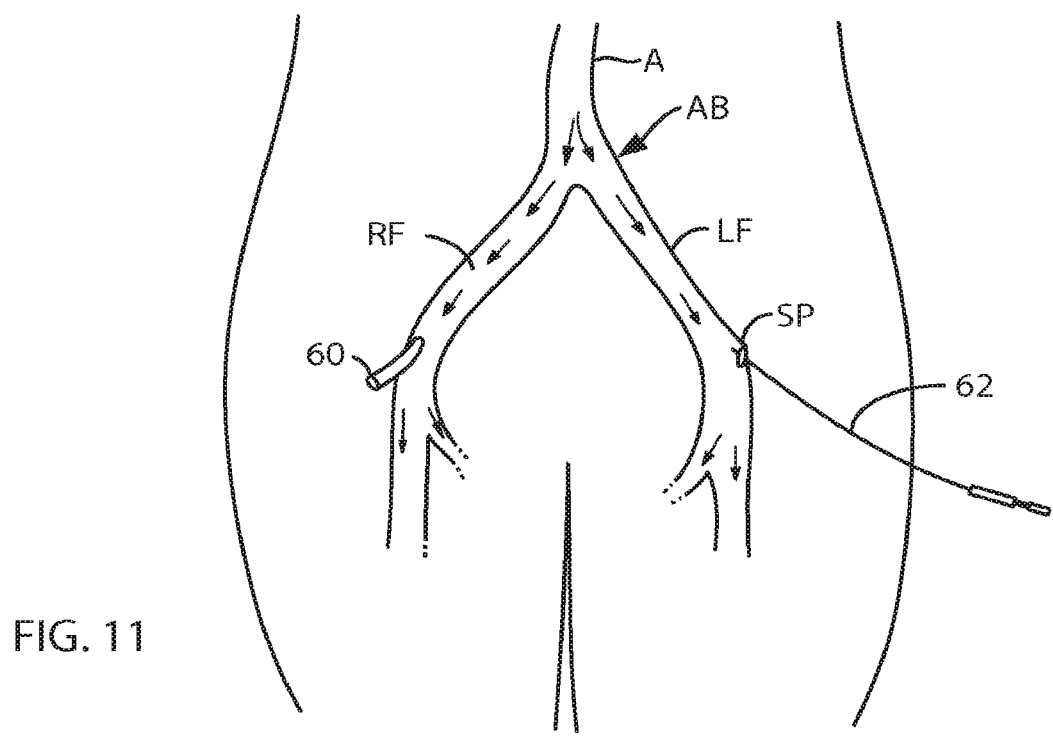

As shown in FIG. 7, while the balloon occlusion element 38 remains inflated, the applicator 16 may be used to inject a tissue adhesive or introduce another sealing material into the tissue tract TT, shown in broken line. After the sealing material has cured or otherwise hardened to form a permanent occlusion or plug, as shown at 60 in FIG. 8, the occlusion catheter 14 may be withdrawn through the access catheter 12, and the access catheter 12 may then be withdrawn through the small diameter sheath SD, as shown in FIG. 9. Blood is then able to flow freely down both the right femoral artery RF and left femoral artery LF. Any conventional vascular closure device may then be used to close the small penetration SP in the left femoral artery. As shown in FIG. 10, a Boomerang® device 62 may be deployed through the small diameter sheath and used to facilitate clotting and closure of the small penetration SP. As shown in FIG. 11 after the small penetration SP has been closed, the Boomerang 62 device may be removed and the patient may go to recovery.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for closing a large penetration in an arterial wall at the end of a tissue tract formed from a skin surface of the patient to the arterial wall, said method comprising:
   advancing an occlusion catheter through a second penetration in the arterial wall to position an occlusion element on a luminal side of the large penetration;
   deploying the occlusion element to temporarily seal the large penetration while allowing blood perfusion past the occlusion element; and
   introducing a sealant into the tissue tract above the large penetration temporarily sealed by the occlusion element such that the sealant is disposed within the tissue tract to promote hemostasis of the tissue tract.

2. The method of claim 1, wherein the large penetration is disposed in a femoral artery and the second penetration is disposed in the contralateral femoral artery.

3. The method of claim 1, additionally comprising advancing an access catheter through the second penetration in the arterial wall.

4. The method of claim 1, additionally comprising allowing the sealant to harden within the tissue tract to permanently occlude the tissue tract, while the occlusion element is deployed to temporarily seal the large penetration.

5. The method of claim 1, additionally comprising allowing blood to perfuse in a direction transverse to a longitudinal axis of the artery into one or more inlet ports on the occlusion catheter, wherein the one or more inlet ports on the occlusion catheter are spaced away from the occlusion element and face outwardly toward the arterial wall.

6. The method of claim 1, wherein the occlusion element is disposed on a distal region of the occlusion catheter.

7. The method of claim 1, wherein the step of introducing the sealant additionally comprises introducing the sealant opposite the luminal side of the large penetration with a distal tip of an applicator, the distal tip being positioned at least partially through the tissue tract and adjacent an outer wall of the artery.

8. The method of claim 1, wherein the sealant comprises a material selected from the group consisting of an adhesive; a thrombotic material; and a hemostatic plug.

9. The method of claim 1, wherein the step of introducing a sealant comprises using an applicator selected from the group consisting of a syringe, a cannula, and a catheter.

10. A system for sealing a large penetration in a wall of a first femoral artery at the end of a tissue tract formed from a skin surface of the patient to the arterial wall, said system comprising:
   an access catheter having a flow diversion element near a distal end thereof;
   an occlusion catheter slidably disposed within the access catheter and having an occlusion element near a distal end thereof, wherein the occlusion element is configured to be radially expanded to temporarily seal the large penetration when placed adjacent thereto within the first femoral artery, wherein the occlusion catheter comprises a sidewall having one or more inlet ports therethrough, and wherein the one or more inlet ports are configured to allow blood perfusion in a direction transverse to a longitudinal axis of the artery; and
   an applicator adapted to deliver a sealing material into the tissue tract above the large penetration temporarily sealed by the occlusion element such that the sealing material is disposed within the tissue tract to promote hemostasis of the tissue tract.

11. The system of claim 10, wherein the access catheter is configured to be disposed through a second penetration in the arterial wall.

12. The system of claim 11, wherein the flow diversion element of the access catheter is configured to be disposed at a location of the artery upstream of the large penetration, wherein the flow diversion element is configured to be radially expanded to inhibit blood flow towards the large penetration.

13. The system of claim 12, wherein the flow diversion element is configured to be radially collapsed to allow blood flow towards the large penetration to resume after the occlusion element is deployed.

14. The system of claim 10, wherein the sealing material is configured to be disposed within the tissue tract and wherein the sealing material is configured to harden and permanently occlude the tissue tract when disposed within the tissue tract while the occlusion element is deployed to temporarily seal the large penetration.

15. The system of claim 10, wherein the one or more inlet ports are spaced away from the occlusion element and wherein the one or more inlet ports are configured to face outwardly toward the arterial wall.

16. The system of claim 11, wherein the access catheter comprises a central passage and wherein the flow diversion element is disposed within the central passage.

17. The system of claim 16, wherein the occlusion catheter is configured to advance through the central passage of the access catheter and through the second penetration in the arterial wall while the flow diversion element is deployed.

18. The system of claim 10, wherein the occlusion element is disposed on a distal region of the occlusion catheter.

19. The system of claim 10, wherein the sealing material comprises a material selected from the group consisting of an adhesive; a thrombotic material; and a hemostatic plug.

20. The system of claim 10, wherein the applicator comprises a device selected from the group consisting of a syringe, a cannula, and a catheter.

* * * * *